United States Patent [19]

Hofen et al.

[11] 4,089,892

[45] May 16, 1978

[54] PROCESS FOR THE PREPARATION OF PERCARBOXYLIC ACID SOLUTIONS

[75] Inventors: Willi Hofen, Rodenbach; Gerd Schreyer; Rolf Wirthwein, both of Hanau; Helmut Waldmann; Gerd Siekmann, both of Leverkusen, all of Germany

[73] Assignees: Deutsche Gold-und Silberscheideanstalt Vormals Roessler, Frankfurt am Main; Bayer Aktiengesellschaft, Leverkusen, both of Germany

[21] Appl. No.: 678,829

[22] Filed: Apr. 28, 1976

[30] Foreign Application Priority Data

Apr. 30, 1975 Germany .................. 2519287

[51] Int. Cl.$^2$ .................. C07C 179/10; B01D 3/00
[52] U.S. Cl. .................. 260/502 R; 203/98; 203/99; 423/589
[58] Field of Search .................. 260/502 R, 50.2; 423/584, 589; 203/14, 98, 99

[56] References Cited

U.S. PATENT DOCUMENTS

| | | | |
|---|---|---|---|
| 2,741,584 | 4/1956 | Holmes et al. | 203/98 |
| 2,814,641 | 11/1957 | Phillips et al. | 260/502 R |
| 3,043,666 | 7/1962 | Siwinski | 423/589 |
| 3,247,244 | 4/1966 | Blumbergs et al. | 260/502 R |
| 3,284,491 | 11/1966 | Korach et al. | 260/502 R |
| 3,341,297 | 9/1967 | MacLean | 423/587 |

FOREIGN PATENT DOCUMENTS

2,262,970  7/1974  Germany .................. 260/502 R

*Primary Examiner*—James O. Thomas, Jr.
*Assistant Examiner*—Werren B. Lone
*Attorney, Agent, or Firm*—Burgess, Dinklage & Sprung

[57] ABSTRACT

Process for continuous production of substantially anhydrous solutions of percarboxylic acid in solvent. Aqueous hydrogen peroxide is first reacted with the corresponding carboxylic acid in the presence of acid catalyst to form percarboxylic acid and water (1). The percarboxylic acid is extracted with solvent (5), to provide a solvent phase containing the percarboxylic acid (11) and an aqueous raffinate (7). The solvent phase is subjected to distillation (12) to provide the anhydrous solution (13). In this distillation (12) the hydrogen peroxide remaining in the solvent phase produced in the extraction (5), is distilled off together with water and some solvent, and the hydrogen peroxide is recovered as an aqueous phase and recycled (14). The aqueous raffinate, which contains hydrogen peroxide, is distilled to remove water (8) and the resulting concentrate is recycled (2) for use in the reaction (1).

17 Claims, 1 Drawing Figure

U.S. Patent     May 16, 1978     4,089,892
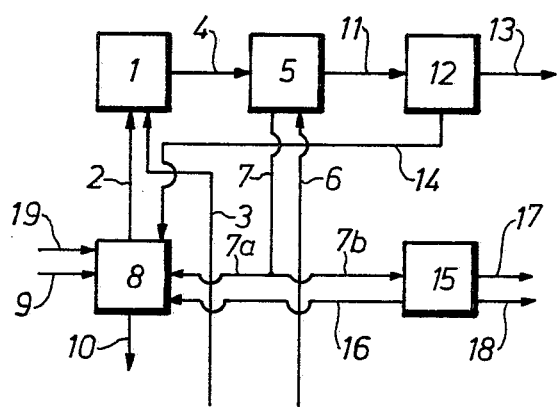

PROCESS FOR THE PREPARATION OF PERCARBOXYLIC ACID SOLUTIONS

The following applications are related to the process hereof for production of propylene oxide as being directed to aspects of the process, some of which are disclosed herein.

| German Ser. No. | U.S. Atty's. Docket No. | U.S. Ser. No. |
| --- | --- | --- |
| P 25 19 288.5 | Bayer 2883 | 678,819 |
| P 25 19 300.4 | Bayer 2884 | 678,820 |
| P 25 19 299.8 | Bayer 2885 | 678,821 |
| P 25 19 298.7–42 | Bayer 2886 | 678,822 |
| P 25 19 297.6 | Bayer 2887 | 678,823 |
| P 25 19 295.4 | Bayer 2888 | 678,824 |
| P 25 19 293.2–42 | Bayer 2889 | 678,825 |
| P 25 19 292.1–42 | Bayer 2890 | 678,826 |
| P 25 19 291.0–42 | Bayer 2891 | 678,826 |
| P 25 19 289.6 | Bayer 2892 | 678,827 |

All of the German applications were filed Apr. 30, 1975. Those applications are incorporated herein by reference.

BACKGROUND

The present invention relates to an improved continuous process for the preparation of anhydrous solutions of percarboxylic acids, with 1–4 carbon atoms, in organic solvents, starting from hydrogen peroxide and carboxylic acids with 1–4 carbon atoms.

Percarboxylic acids have become increasingly important in the reaction of olefines to give epoxides (D. Swern, "Organic Peroxides," Wiley Interscience 1971, Vol. II, page 360 II.) and of cyclic ketones to give lactones (Houben-Weyl "Methoden der organischen Chemie" (Methods of Organic Chemistry) Volume IV/2, page 708).

However, the aqueous solutions of percarboxylic acids with 2–4 carbon atoms, which are readily accessible, for example according to German Pat. Nos. 1,165,576 and 1,170,926, are not suitable for these reactions in all cases due to the presence of water, since water promotes opening of the ring in the products obtained in the reaction. On the other hand, anhydrous or substantially anhydrous solutions of percarboxylic acids give excellent results (see loc. cit.).

The synthesis of anhydrous or substantially anhydrous solutions of percarboxylic acids in organic solvents is known (see Ullmann, Enzyklopadie der Technischen Chemie (Encyclopaedia of Industrial Chemistry), supplementary volume 1970, Neue Verfahren (New Processes), page 181 et seq. and Swern, Organic Peroxides I, 1970, page 313 et seq.).

These solutions can be obtained, for example, by autoxidation of aldehydes in an anhydrous medium, for example in carboxylic acid esters.

This method has the disadvantage that explosive intermediate products can form in this process and that the carboxylic acid corresponding to the aldehyde is obtained as a by-product after the reaction of the peracid, for example with an olefine.

Organic solutions of percarboxylic acids are also obtained by the reaction of hydrogen peroxide with carboxylic acids in the presence of an acid catalyst, according to equation (1)

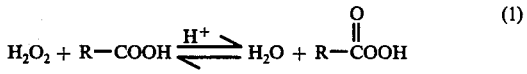

$$H_2O_2 + R\text{—}COOH \underset{}{\overset{H^+}{\rightleftharpoons}} H_2O + R\text{—}\overset{\overset{O}{\|}}{C}OOH \quad (1)$$

when the reaction is carried out in the presence of an organic solvent and the water is removed by azeotropic distillation (see DT-AS (German published specification) No. 1,043,316, U.S.A. Pat. No. 2,877,266 and DT-OS (German published specification) No. 1,917,032). However, it is also possible first to prepare an anhydrous solution of hydrogen peroxide in an organic solvent and then to react this with a carboxylic acid in the presence of an acid catalyst (see DTOS (German published specification) No. 2,038,318).

Furthermore, organic solutions of percarboxylic acids can be prepared by discontinuous or continuous extraction of pure aqueous percarboxylic acid solutions with organic solvents, for example carboxylic acid esters, phosphoric acid esters and chlorinated or aromatic hydrocarbons, and subsequent azeotropic dehydration of the resulting extracts or also solely by azeotropic dehydration of the aqueous percarboxylic acid solutions. In this case, part of the organic solvent employed is used to dilute the percarboxylic acid (DT-OS (German published specification) No. 2,141,155, DT-OS (German published specification) No. 2,141,156 and DT-OS (German published specification) No. 2,145,604).

Other processes for the preparation of anhydrous solutions of percarboxylic acids are based on the extraction, with organic solvents, of the equilibrium mixture which is set up according to equation (1) and which consists of hydrogen peroxide, carboxylic acid, water and percarboxylic acid and which may still contain the acid catalyst (DT-OS (German published specification) No. 2,141,156, DT-OS (German published specification) No. 1,048,569 and DT-OS (German published specification) No. 1,618,625).

In these processes, the extractions to obtain anhydrous percarboxylic acid solutions are carried out either in several stages or in one stage. In every case the raffinate, which, regarded from the total preparation of the percarboxylic acid, still contained considerable amounts of hydrogen peroxide and possibly of the acid catalyst, was discarded and these substances were thus lost.

However, processes have also been disclosed according to which the raffinates obtained can be worked up in order to recover the amounts of hydrogen peroxide or acid catalysts contained therein and to recycle these to the reaction of hydrogen peroxide with carboxylic acid.

Thus, unreacted hydrogen peroxide contained in the raffinate can be destroyed according to known methods and the acid catalyst can be recovered (DT-OS (German published specification) No. 2,312,281).

According to another process, aqueous hydrogen peroxide is first reacted, according to equation (1), with a carboxylic acid with 2–4 carbon atoms, in the presence of an acid catalyst, it being possible for the molar ratio of hydrogen peroxide/carboxylic acid employed to be 0.5–30:1. The reaction mixture is extracted in counter-current with an organic solvent and the extract, which may have been further treated with water, is dehydrated by azeotropic distillation. The aqueous raffinate obtained from the extraction of the reaction mixture with an organic solvent contains both unreacted hydrogen peroxide and also the acid catalyst. These can be recovered and recycled into the reaction stage by feeding the raffinate to an evaporator unit and distilling off, under reduced pressure, the water introduced with the starting materials and formed by the reaction according to equation (1) and recycling the raffinate concentrated in this way into the reaction of hydrogen peroxide with the carboxylic acid. In some cases it also suffices to work up only a part of the raffinate in the manner described. The hydrogen peroxide consumed after the reaction according to equation (1) is replenished after concentrating the raffinate. According to this process, the yields of percarboxylic acids are 87 – 90.5%, relative to hydrogen peroxide employed (DT-OS (German published specification) No. 2,262,970).

The Invention

The present invention is based on a number of surprising findings in the preparation of anhydrous or substantially anhydrous solutions of percarboxylic acids, especially permonocarboxylic acids, with 1 – 4 carbon atoms, in organic solvents by the reaction of hydrogen peroxide with the corresponding carboxylic acids with 1-4 carbon atoms, which findings lead to a substantial improvement in the yields of percarboxylic acids.

The process according to the invention for the continuous preparation of anhydrous or substantially anhydrous solutions of percarboxylic acids with 1 – 4 carbon atoms by reacting aqueous hydrogen peroxide with carboxylic acids in the presence of acid catalysts, employing a molar ratio of hydrogen peroxide: carboxylic acid of 0.5 – 30:1, extracting the reaction solution in counter-current with organic solvents, isolating a substantially anhydrous solution of the percarboxylic acid as the extract, dehydrating the extract by azeotropic distillation, distilling off water, under reduced pressure, from the entire aqueous raffinate or from a part thereof, recycling the raffinate reconcentrated in this way, as well as the part of the raffinate which optionally is not worked up, into the reaction stage and replenishing with amounts of aqueous hydrogen peroxide and carboxylic acid such that the initial state is restored, is characterized in that (a) the total aqueous raffinate from the extraction of the reaction mixture, or a part thereof, together with the total amount of hydrogen peroxide employed, or a partial amount thereof, is fed to an evaporator unit and the water introduced with the aqueous hydrogen peroxide solution and formed during the reaction is distilled off under reduced pressure, (b) part of the raffinate from the extraction of the reaction mixture, or part of the reconcentrated raffinate, is withdrawn discontinuously or continuously, the hydrogen peroxide contained therein is largely recovered and recycled into the process and the amount of acid catalyst removed by the withdrawal is replenished, and (c) when dehydrating the extract from the extraction of the reaction mixture by azeotropic distillation, the amount of solvent in the distillate is regulated so that, after the phase separation, the hydrogen peroxide which still remained in the extract is obtained, together with water, as the distillate and that this aqueous hydrogen peroxide is recycled into the process.

By means of the combination of the measures according to the invention which are described above, a quite considerable increase in the yield of percarboxylic acid is achieved.

Steps (a) and (b) — treatment of aqueous raffinate.

The raffinate which is obtained from the extraction of the reaction mixture and which essentially consists of water, hydrogen peroxide and acid catalyst, is concentrated in a known manner by distillation (DT-OS (German published specification) No. 2,262,970).

All or part of the amount of aqueous hydrogen peroxide necessary to maintain the reaction, according to the process of the invention, is fed together with all or part of the raffinate from the extraction of the reaction mixture to a rectification unit, which generally consists of a reboiler, a column and a condenser. The aqueous hydrogen peroxide solution can either be passed directly into the evaporator or can previously be mixed with the raffinate and then passed into the evaporator unit. In the rectification unit, the water formed during the reaction and introduced with the hydrogen peroxide is distilled off under reduced pressure.

The residence time in the sump of the evaporator unit is restricted to 3–30 minutes and the sump temperature is restricted to 40°–120° C, preferably 60°–85° C. The pressure is 10–250 mm Hg, preferably 50–150 mm Hg. On prolonged continuous operation of the process, impurities accumulate after a certain time in the acid aqueous hydrogen peroxide solution which is obtained as the raffinate from the extraction of the reaction mixture and these impurities promote the decomposition of the percarboxylic acids and of the hydrogen peroxide. In order to keep the concentration of the impurity at a constant level it is necessary to withdraw part of the raffinate continuously or discontinuously. The fraction of the raffinate which is withdrawn hourly depends on the loss of active oxygen per unit time and must be determined from case to case. In general, because of the losses of hydrogen peroxide associated therewith, the raffinate withdrawn cannot be discarded. In order to recover the hydrogen peroxide contained in the raffinate which has been withdrawn, this raffinate is passed to a recovery unit for hydrogen peroxide. This consists of a pre-heater, a column and a condenser. The distillation column has, in its lower part, a bubble cap tray without a downcomer, so that whilst vapor can flow away into the upper part of the column, the reflux collects on the bubble cap tray. To separate the hydrogen peroxide from the solution which is withdrawn, this solution is heated in the preheater and fed, below the bubble cap tray without a downcomer, to the column which operates under vacuum. At the same time, steam is passed in at the sump of the column. At the top of the column in the main water condenses and a small reflux is passed to the column. The hydrogen peroxide stripped off is enriched in the upper part of the column and is withdrawn as an aqueous solution from the bubble cap tray without a downcomer. Since the hydrogen peroxide recovered in this way is generally more dilute, for example 10 – 20% strength by weight, than that employed in the process this hydrogen peroxide is passed to reconcentration. The dilute solution of the acid catalyst which collects in the sump of the column is discarded.

The distillation column is operated at a pressure of 25 – 250 mm Hg. The temperature in the preheater for the column is 30° – 120° C, preferably 80° – 100° C.

Since with this type of hydrogen peroxide recovery part of the acid catalyst is lost, this must be replenished. This can be effected either direct by addition into the evaporator unit of by addition to the raffinate from the extraction of the reaction mixture upstream or downstream of the evaporator unit. It is also possible to add the amount of acid catalyst to be replenished to the make-up hydrogen peroxide solution to be fed in before entry into the evaporator unit.

Step (c) — dehydration of the extract

The reaction mixture which is formed according to equation (1) is extracted in a known manner with an organic solvent. The extract obtained contains, in addition to benzene, perpropionic acid, propionic acid, hydrogen peroxide, water and possibly small amounts of the acid catalyst. The extract generally contains 0.2 – 1% of hydrogen peroxide.

In order to separate off the water and the hydrogen peroxide from the extract, this is passed to a rectification unit consisting of a reboiler, a column and a condenser. After the phase separation, an aqueous hydrogen peroxide solution is obtained as the distillate, whilst the organic solvent is returned to the column as reflux. An amount of solvent greater than that corresponding to the water content is evaporated. The distillation is preferably carried out at 100 – 400 mm Hg. The sump temperature should be lower than 80° C, preferably lower than 70° C.

The amount of solvent evaporated during the distillation is about 1.5 to 40 times the amount of solvent required for the azeotropic distillation of the water content of the extract of the reaction mixture. The hydrogen peroxide recovered in this way, which contains 0.5 – 30% by weight of hydrogen peroxide, is recycled into the process.

Embodiments

Aliphatic carboxylic acids with up to 4 carbon atoms, especially propionic acid, are particularly suitable for the process according to the invention. Sulphuric acid is preferably used as the acid catalyst. The other conditions correspond to those in DT-OS (German published specification) No. 2,262,970.

The present invention is illustrated by the example which follows.

Example (see also FIG. 1)

In continuous operation, 20.12 kg ( $\triangleq$ 271 mols) of propionic acid (99.8% strength by weight, stream 3) and 29.94 kg of an aqueous solution (product stream 2) which on average contains 29.4% by weight of hydrogen peroxide ($\triangleq$ 259 mols), 33.0% by weight of sulphuric acid and 7.5% by weight of Caro's acid, are pumped per hour through the reaction system 1 consisting of a two-stage stirred kettle cascade. The molar ratio of hydrogen peroxide to propionic acid is 1.03 : 1, the hydrogen peroxide bonded in the Caro's acid being calculated as free $H_2O_2$.

With an average residence time of 28 minutes in the stirred kettle cascade and at a reaction temperature of 35° C, a reaction mixture (50.06 kg/hour) which contains, on average, 28.0% by weight of perpropionic acid, 17.1% by weight of propionic acid, 7.0% by weight of hydrogen peroxide, 19.7% by weight of sulphuric acid, 4.5% by weight of Caro's acid and 23.7% by weight of water, is obtained. This reaction mixture (product stream 4) is fed to the extraction system 5 of a pulsed sieve tray column.

45.75 kg per hour of benzene (stream 6), which contains 0.11% by weight of propionic acid and 0.09% by weight of water, are fed into the column as the extraction agent. At the upper end of the column, 69.26 kg per hour of benzene extract (product stream 11), which contains, on average, 20.19% by weight of perpropionic acid, 12.41% by weight of propionic acid, 0.58% by weight of hydrogen peroxide and 0.92% by weight of water, are withdrawn.

The aqueous raffinate from the extraction (product stream 7) is withdrawn at the lower end of the column in an amount of 26.55 kg/hour. This raffinate contains, on average, 11.74% by weight of hydrogen peroxide, 37.12% by weight of sulphuric acid, 8.49% by weight of Caro's acid as well as 0.10% by weight of perpropionic acid and 0.06% by weight of propionic acid.

A small partial stream of the raffinate (product stream 7b) of 0.87 kg/hour ( $\triangleq$ 3.3%) is withdrawn and worked up separately.

The bulk of the raffinate (product stream 7a), 25.68 kg.hour, is again made up for renewed reaction with propionic acid by passing it, together with 11.0 kg/hour of 50% strength by weight aqueous hydrogen peroxide ( $\triangleq$ 161.7 mols/hour of $H_2O_2$ employed, stream 9), a further 0.52 kg/hour of 17% strength by weight aqueous hydrogen peroxide (product stream 16) and 1.0 kg/hour of 32.3% strength by weight aqueous hydrogen peroxide (product stream 14) as well as 0.41 kg/hour of sulphuric acid (95% strength by weight, stream 19, as replacement for the loss of the $H_2SO_4$ contained in product stream 7b), to a distillation unit 8 and reconcentrating the mixture thus obtained by distilling off water.

The distillation unit 8 consists of a packed column (length = 4m, diameter = 150 mm), a condenser and a falling film evaporator made of zirconium ("commerical grade"). The mixture of the product streams 7a, 9, 16, 14 and 19 is passed directly to the evaporator. With a residence time of 12 minutes in the sump of the column, at a pressure of 50 mm Hg, a sump temperature of 68° – 69° C, a temperature at the top of the column of 36° – 37° C and with a reflux ratio of 0.55, 8.60 kg per hour of water, which still contains 0.05% by weight of hydrogen peroxide as well as 0.53% by weight of perpropionic acid and 0.38% by weight of propionic acid, (product stream 10) are distilled off. 29.94 kg per hour of product stream 2 are withdrawn from the sump of the column and fed back to the reaction system 1.

The raffinate (product stream 7b), 0.87 kg/hour, withdrawn from the aqueous cycle is worked up in a distillation unit 15. This consists of a packed column (length = 4 m, diameter = 100 mm), which, above the feedpoint located in the centre, possesses a take-off weir for withdrawing a sidestream. The column is also provided with a preheater for the feed. The column is operated at a pressure of 50 mm Hg, a temperature at the top of 38° C and a reflux ratio of 0.1. The temperature in the preheater is 50° C.

5.5 kg of steam per hour are blown in above the sump. 0.52 kg per hour of 17% strength by weight aqueous hydrogen peroxide are withdrawn from the column as a side stream (product stream 16) and fed to the distillation unit 8. In addition, 4.87 kg/hour of water with 0.04% by weight of hydrogen peroxide (product stream 17) are obtained as the distillate and 0.98 kg/hour of an aqueous solution (product stream 18), which contains 1.2% by weight of hydrogen peroxide, 32.9% by weight of sulphuric acid and 7.5% by weight of Caro's acid, are obtained in the sump.

The benzene extract (product stream 11) withdrawn from the extraction column 5 is passed, together with a solution of a stabilizer, to the azeotropic distillation 12. A sodium salt of a partially esterified polyphosphoric acid is used as the stabilizer and is added as a 15% strength by weight solution in propionic acid (0.11 kg/hour).

The distillation unit 12 consists of a packed column (length = 3 m, diameter = 200 mm), a falling film evaporator, a condenser and a separator for phase separation of the distillate at the top of the column. The product stream 11 is fed into the lower part of the column. At a pressure of 300 mm Hg and a temperature at the top of the column of 46° – 48° C, 1.0 kg of aqueous phase and about 66 kg of benzene phase are obtained per hour as the distillate. The benzene phase is returned to the column as reflux whilst the aqueous phase (product stream 14), which contains 32.3% by weight of hydrogen peroxide, 2.0% by weight of perpropionic acid and 1.7% by weight of propionic acid, is passed into the distillation unit 8. The amount of benzene distilled corresponds to about 8 times the amount that would be required for azeotropic separation of the water from the product stream 11.

68.37 kg per hour of a benzene solution of perpropionic acid (20.42% by weight ≙ 155.0 mols/hour), which also contains 12.69% by weight of propionic acid, 0.09% by weight of hydrogen peroxide, 0.02% by weight of water and the abovementioned stabilizer, (product stream 13) are obtained as the sump product of this azeotropic distillation.

The yield of perpropionic acid in the dried benzene solution is 95.8%, relative to the amount of hydrogen peroxide charged to the process (product stream 9).

What is claimed is:

1. In a process for the continuous production of a substantially anhydrous solution of a percarboxylic 1-4 carbon atoms in organic solvent selected from the group consisting of carboxylic acid esters, phosphoric acid esters chlorinated hydrocarbons, and aromatic hydrocarbons which comprises contacting aqueous hydrogen peroxide with the corresponding carboxylic acid in the presence of an acid catalyst for the reaction to produce the percarboxylic acid and water, the molar ratio of hydrogen: carboxylic acid during a said contacting being 0.5-30:1, extracting the mixture with the organic solvent for formation of a solvent phase rich in percarboxylic acid and carboxylic acid and containing hydrogen peroxide, and an aqueous raffinate phase rich in hydrogen peroxide and acid catalyst, dehydrating said solvent phase by distillation, distilling at least part of the aqueous raffinate of the solvent extraction under reduced pressure to remove water therefrom and form concentrated solution of hydrogen peroxide and catalyst, recycling said concentrated solution and any part of the aqueous raffinate which is not distilled to said contacting of hydrogen peroxide and carboxylic acid, and introducing make-up hydrogen peroxide as aqueous hydrogen peroxide, and make-up carboxylic acid into said contacting, the improvement which comprises:

in said dehydration of the solvent phase by distillation, distilling off solvent containing water and hydrogen peroxide as overhead product of the distillation, while distilling over an amount of solvent in said over head which is 1.5-40 times the amount required for azeotropic distillation of the water, and withdrawing as bottom product of the distillation said substantially anhydrous solution, condensing said overhead product for formation of two phases, including an aqueous phase containing hydrogen peroxide, and recycling said aqueous phase for use in said contacting, the amount of solvent distilled off in the overhead product being such that the hydrogen peroxide contained in the solvent phase produced in said extraction, is contained in the aqueous phase containing hydrogen peroxide produced in said condensation.

2. Process of claim 1, wherein the aqueous raffinate distillation is performed at 10-250 mm Hg pressure.

3. Process of claim 1, wherein said aqueous raffinate distillation is performed at 50-150 mm Hg.

4. Process of claim 1, wherein said make-up acid catalyst is introduced directly into the evaporator unit of step (a), is admixed with the aqueous raffinate upstream or downstream of said evaporator unit, or is admixed with make-up aqueous hydrogen peroxide solution introduced into the evaporator unit.

5. Process of claim 1, wherein, in step (a), the residence time in the sump of the evaporator unit is 3-30 minutes, and the sump temperature is 40°-120° C.

6. Process of claim 1, wherein, in step (b), said separation is performed in a recovery unit comprising a preheater, a column with a bubble cap tray without a downcomer, and a condenser, and the separation is by distillation at reduced pressure.

7. Process of claim 6, wherein the aqueous hydrogen peroxide recovered in step (b) is recycled to step (a).

8. Process according to claim 6, wherein the column of the recovery unit is operated at a pressure of 25-250 mm Hg and wherein the preheater heats the feed to the column to 30°-120° C.

9. Process of claim 1, wherein the aqueous hydrogen peroxide phase produced in step (c) is recycled to step (a).

10. Process of claim 1, wherein percarboxylic acid is perpropionic acid, the distillation of step (a) is performed at 10-250 mm Hg.

11. Process of claim 1, wherein in step (c), the second phase produced by said condensation is an organic phase and said organic phase is employed as reflux for the distillation.

12. Process of claim 1, wherein the extraction with organic solvent is countercurrent.

13. Process of claim 1, wherein the dehydration performed in step (c) is at 100-400 mm Hg, and a sump temperature of lower than 80° C.

14. Process of claim 13, wherein the percarboxylic acid is perpropionic acid, the catalyst is sulfuric acid and the solvent is benzene.

15. A process according to claim 1 wherein at least part of the make-up aqueous hydrogen peroxide together with the aqueous raffinate subjected to the aqueous raffinate distillation is introduced into an evaporator unit for said distillation of said aqueous raffinate, wherein the water introduced into the process with the make-up hydrogen peroxide, and the water formed during said contacting is distilled off under said reduced pressure.

16. A process according to claim 1 wherein a portion of the aqueous raffinate or a portion of the concentrated solution formed in the aqueous raffinate distillation is withdrawn and separated into a hydrogen peroxide rich phase and an acid catalyst rich phase, the hydrogen peroside rich phase is recycled to the process for use in said contacting, the acid catalyst rich phase is withdrawn from the process and make-up acid catalyst is introduced into the process for use in said contacting.

17. A process according to claim 15 wherein a portion of the aqueous raffinate or a portion of the concentrated solution formed in the aqueous raffinate distillation is withdrawn and separated into a hydrogen peroxide rich phase and an acid catalyst rich phase, the hydrogen peroxide rich phase is recycled for use in said contacting, the acid catalyst rich phase is withdrawn from the process and make-up acid catalyst is introduced into the process for use in said contacting.

* * * * *